US011328820B2

(12) United States Patent
Griffin et al.

(10) Patent No.: US 11,328,820 B2
(45) Date of Patent: May 10, 2022

(54) DECISION ENGINE BASED ON DISPARATE DATA SOURCES

(71) Applicant: Doctor on Demand, Inc., San Francisco, CA (US)

(72) Inventors: Kent Griffin, San Francisco, CA (US); Alejandro Novoa, San Francisco, CA (US); Andrew Chang, San Francisco, CA (US); Travis Swientek, San Francisco, CA (US); Greg Corey, San Francisco, CA (US); Todd Kusterer, San Francisco, CA (US)

(73) Assignee: DOCTOR ON DEMAND, INC., San Francisco, CA (US)

( * ) Notice: Subject to any disclaimer, the term of this patent is extended or adjusted under 35 U.S.C. 154(b) by 143 days.

(21) Appl. No.: 16/855,932

(22) Filed: Apr. 22, 2020

(65) Prior Publication Data
US 2021/0257093 A1    Aug. 19, 2021

Related U.S. Application Data

(60) Provisional application No. 62/977,096, filed on Feb. 14, 2020.

(51) Int. Cl.
*G16H 50/20* (2018.01)
*G16H 10/60* (2018.01)
*G16H 40/40* (2018.01)
*G16H 50/30* (2018.01)

(52) U.S. Cl.
CPC .......... *G16H 50/20* (2018.01); *G16H 10/60* (2018.01); *G16H 40/40* (2018.01); *G16H 50/30* (2018.01)

(58) Field of Classification Search
CPC ........ G16H 50/20; G16H 10/60; G16H 50/30; G16H 40/40
USPC .......................................................... 705/3
See application file for complete search history.

(56) References Cited

U.S. PATENT DOCUMENTS

| 8,185,461 | B2* | 5/2012 | Kenedy | G16H 70/20 |
| | | | | 705/35 |
| 8,788,286 | B2* | 7/2014 | Kenedy | G16H 50/20 |
| | | | | 705/2 |
| 2004/0077955 | A1* | 4/2004 | Kawanishi | A61B 5/02116 |
| | | | | 600/483 |
| 2017/0185733 | A1* | 6/2017 | Nogueira | A61B 5/14735 |
| 2019/0042618 | A1* | 2/2019 | Potulska | G06F 16/2365 |
| 2019/0043618 | A1* | 2/2019 | Vaughan | G16H 50/20 |
| 2020/0176098 | A1* | 6/2020 | Lucas | G16H 70/40 |

* cited by examiner

*Primary Examiner* — Michael Tomaszewski
*Assistant Examiner* — Rachael Sojin Stone
(74) *Attorney, Agent, or Firm* — Haynes and Boone, LLP

(57) ABSTRACT

Systems and methods for medical intervention using machine learning techniques are provided. One or more embodiments include receiving data associated with a medical condition from a user. Based on the user, a patient profile is retrieved from a database. An intervention is determined for the medical condition based on a patient history provided as an input to a machine learning model that recommends interventions. The intervention is sent to a user device associated with the user. Changes are monitored in one or more health metrics associated with the user. The machine learning models are re-trained based on the monitored changes and the intervention.

20 Claims, 5 Drawing Sheets

DECISION ENGINE BASED ON DISPARATE DATA SOURCES

CROSS REFERENCE TO RELATED APPLICATIONS

This application claims priority to U.S. Patent Application No. 62/977,096, filed Feb. 14, 2020, which is incorporated by reference herein in its entirety.

TECHNICAL FIELD

The present disclosure generally relates to machine intelligence and more particularly to healthcare intervention utilizing machine intelligence and disparate data sources according to various embodiments.

BACKGROUND

The distribution of health-related services and information via the internet allows for long-distance healthcare. As the internet becomes more prevalent for health-related services, there will be a growing volume of data exchanged between various health care providers. As the volume of exchanged data grows, the less feasible it becomes for humans to evaluate the data. Thus, there is a need for an improvement in the field of healthcare data management and related technology to observe, evaluate, and make decisions using machines capable of advanced machine learning techniques.

Figure 1:
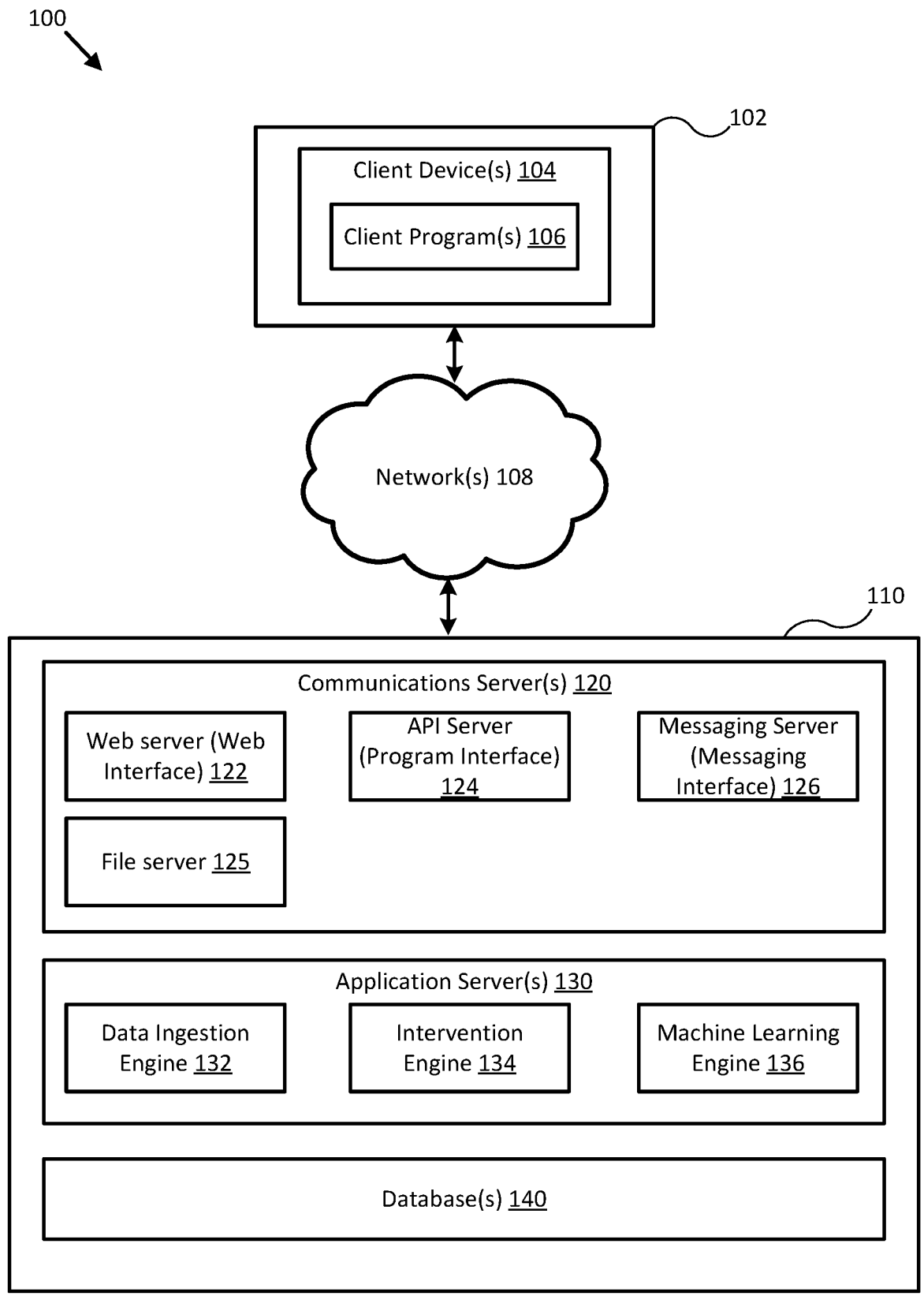
FIG. 1 illustrates a block diagram of a networked system suitable for implementing one or more embodiments of the present disclosure.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

The detailed description set forth below is intended as a description of various configurations of the subject technology and is not intended to represent the only configurations in which the subject technology can be practiced. The appended drawings are incorporated herein and constitute a part of the detailed description. The detailed description includes specific details for the purpose of providing a thorough understanding of the subject technology. However, it will be clear and apparent to those skilled in the art that the subject technology is not limited to the specific details set forth herein and may be practiced using one or more embodiments. In one or more instances, structures and components are shown in block diagram form in order to avoid obscuring the concepts of the subject technology. One or more embodiments of the present disclosure are illustrated by and/or described in connection with one or more figures and are set forth in the claims.

The present disclosure describes systems and methods for healthcare data management that utilize machine learning to systematically process large volumes of data, extract relevant information from the data, and generate insights, predictions and recommendations related to healthcare for patients.

In some embodiments, a system obtains data files from various health care service providers. The data files may be parsed according to their respective file types and further processed to extract specific types of information. Each type of information may be loaded into a database table according to the type of data. Machine learning models may be used to process the data in the database tables to procure insights and predictions that may be employed to control certain automated processes. For example, one or more interventions, recommendations, notifications, and/or in-application graphical user interface activities may be automatically generated for a user based on the insights and/or predictions from the machine learning models.

In some embodiments, health metrics for the user may be measured and/or determined during a monitoring period to evaluate how effective the interventions, recommendations, and/or notifications were in changing the user's health profile. For example, if the user was determined to have a significant health risk for a disease, health metrics that are pertinent to that disease would be monitored after an intervention is provided to the user to determine how effective the intervention was in changing the health risk of the user for that disease.

In various embodiments, the health metrics of the user during and at the end of the monitored time period may be tracked to determine trends in the health metric (e.g., increased, decreased, remained the same). The trends may provide insight as to how the interventions may be adjusted to provide better outcomes. The trends and outcomes may be used as part of training datasets to train machine learning models to better predict interventions in the future for other patients who may share the same or similar medical condition and/or health metrics.

FIG. 1 illustrates an exemplary embodiment of a computing system adapted for implementing one or more embodiments disclosed herein. As shown, a computing system 100 may comprise or implement a plurality of servers, devices, and/or software components that operate to perform various methodologies in accordance with the described embodiments. Exemplary servers, devices, and/or software components may include, for example, stand-alone and enterprise-class servers running an operating system (OS) such as a MICROSOFT® OS, a UNIX® OS, a LINUX® OS, or other suitable OS. It will be appreciated that the servers illustrated in FIG. 1 may be deployed in other ways and that the operations performed and/or the services provided by such servers may be combined, distributed, and/or separated for a given implementation and may be performed by a greater number or fewer number of servers. One or more servers may be operated and/or maintained by the same or different entities.

Computing system 100 may include, among various devices, servers, databases and other elements, one or more clients 102 comprising or employing one or more client devices 104, such as a laptop, a personal computing device, a mobile computing device, a tablet, a smart phone, an electronic wearable device (e.g., smart watch, virtual reality headset, wearable body monitoring device), medical devices for monitoring health metrics, or other similar devices that a user may user and readily access. As a further example, client device 104 may be a fingertip monitoring device, heart rate monitoring device, blood pressure monitoring device, electrocardiogram (EKG) monitor, weight scale, wearable air filtration device, glucometer, ultrasound device, smart utensil, and/or any other healthcare device suitable for measuring one or more health metrics of a user.

Client devices 104 generally may provide one or more client programs 106, such as system programs and application programs to perform various computing and/or communications operations. Exemplary system programs may include, without limitation, an operating system (e.g., MICROSOFT® OS, UNIX® OS, LINUX® OS, Symbian OS™, iOS, macOS, Android, Embedix OS, Binary Runtime Environment for Wireless (BREW) OS, JavaOS, a Wireless Application Protocol (WAP) OS, and others), device drivers, programming tools, utility programs, software libraries, application programming interfaces (APIs), and so forth. Exemplary application programs may include, without limitation, a healthcare application, web browser application, messaging application, contacts application, calendar application, electronic document application, database application, media application (e.g., music, video, television), location-based services (LBS) application (e.g., GPS, mapping, directions, positioning systems, geolocation, point-of-interest, locator) that may utilize hardware components such as an antenna, and so forth. One or more of client programs 106 may display various graphical user interfaces (GUIs) to present information to and/or receive information from one or more users of client devices 104. In some embodiments, client programs 106 may include one or more applications configured to conduct some or all of the functionalities and/or processes discussed below.

As shown, client devices 104 may be communicatively coupled via one or more networks 108 to a network-based system 110. Network-based system 110 may be structured, arranged, and/or configured to allow client 102 to establish one or more communications sessions between network-based system 110 and various client devices 104 and/or client programs 106. Accordingly, a communications session between client devices 104 and network-based system 110 may involve the unidirectional and/or bidirectional exchange of information and may occur over one or more types of networks 108 depending on the mode of communication. While the embodiment of FIG. 1 illustrates a computing system 100 deployed in a client-server operating environment, it is to be understood that other suitable operating environments and/or architectures may be used in accordance with the described embodiments.

Data communications between client devices 104 and the network-based system 110 may be sent and received over one or more networks 108 such as the Internet, a Wide Area Network (WAN), a wireless WAN (WWAN), a wireless Local Area Network (WLAN), a mobile telephone network, a landline telephone network, personal area network, as well as other suitable networks. For example, client devices 104 may communicate with network-based system 110 over the Internet or other suitable WAN by sending and or receiving information via interaction with a website, e-mail, instant message (IM) session, and/or video messaging session. Any of a wide variety of suitable communication types between client devices 104 and system 110 may take place, as will be readily appreciated. In particular, wireless communications of any suitable form (e.g., Bluetooth, near-field communication, etc.) may take place between client device 104 and system 110, such as that which often occurs in the case of mobile phones or other personal and/or mobile devices.

Network-based system 110 may comprise one or more communications servers 120 to provide suitable interfaces that enable communication using various modes of communication and/or via one or more networks 108. Communications servers 120 may include a web server 122, an API server 124, a file server 125, and/or a messaging server 126 to provide interfaces to one or more application servers 130. Application servers 130 of network-based system 110 may be structured, arranged, and/or configured to provide various online services to client devices that communicate with network-based system 110. In various embodiments, client devices 104 may communicate with application servers 130 of network-based system 110 via one or more of a web interface provided by web server 122, a programmatic interface provided by API server 124, and/or a messaging interface provided by messaging server 126. It may be appreciated that web server 122, API server 124, file server 125, and messaging server 126 may be structured, arranged, and/or configured to facilitate communication with various types of client devices 104, and/or client programs 106 and may interoperate with each other in some implementations.

Web server 122 may be arranged to communicate with web clients and/or applications such as a web browser, web browser toolbar, desktop widget, mobile widget, web-based application, web-based interpreter, virtual machine, mobile applications, and so forth. API server 124 may be arranged to communicate with various client programs 106 comprising an implementation of API for network-based system 110. Messaging server 126 may be arranged to communicate with various messaging clients and/or applications such as e-mail, IM, SMS, MMS, telephone, VoIP, video messaging, IRC, and so forth, and messaging server 126 may provide a messaging interface to enable access by client 102 to the various services and functions provided by application servers 130. File server 125 may be arranged to allow a client to connect to file server 125 to upload files to be stored on file server 125 (e.g., cloud storage server) or to download files that are already stored on the server. In some cases, operation of file server 125 may include utilization of Secure File Transfer Protocol (SFTP). SFTP is typically faster than other protocols because the data transfer is more compact as SFTP is packet-based.

Application servers 130 of network-based system 110 may be servers that provide various services to client devices, such as tools for uploading various data files and receiving interventions, recommendations, device instructions and so forth as further described herein. Application servers 130 may include multiple servers and/or components. For example, application servers 130 may include a data ingestion engine 132, intervention engine 134, and machine learning engine 136. These servers and/or components, which may be in addition to other servers, may be structured and arranged to various tasks further described herein.

Application servers 130 may be coupled to and capable of accessing one or more databases 140. Databases 140 generally may store and maintain various types of information for use by application servers 130 and may comprise or be implemented by various types of computer storage devices (e.g., servers, memory) and/or database structures (e.g., relational, object-oriented, hierarchical, dimensional, network) in accordance with the described embodiments. In some embodiments, databases 140 may include several database tables corresponding to specific types of information related to healthcare patients. Machine intelligence may analyze the database tables to determine insights about the patient population and determine interventions to improve or treat the health conditions of groups of patients who have particular medical conditions.

Figure 2:
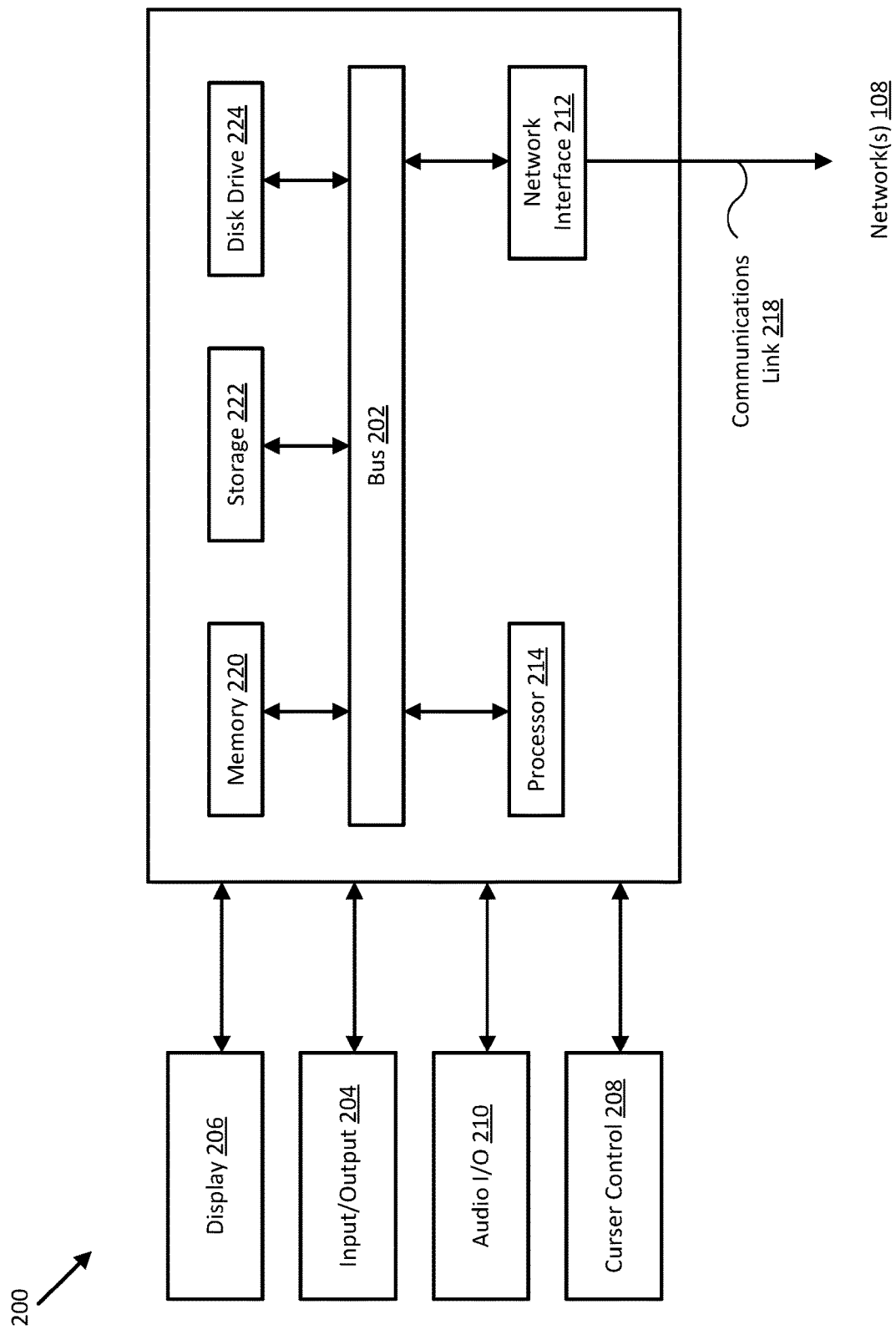
FIG. 2 illustrates a block diagram of a computer system in accordance with one or more embodiments of the present disclosure.

FIG. 2 illustrates an exemplary computer system 200 in block diagram format suitable for implementing one or more devices of the computing system in FIG. 1. In various implementations, a device that includes computer system 200 may comprise a personal computing device (e.g., a smart or mobile phone, a computing tablet, a personal computer, laptop, wearable device, PDA, healthcare monitoring or measurement device, any applicable device discussed herein) that is capable of communicating with a network. A service provider may utilize a network computing device (e.g., a network server) capable of communicating with the network. It should be appreciated that each of the devices utilized by users and service providers may be implemented as computer system 200 in a manner as follows. Additionally, as more and more devices become communication capable, such as smart devices using wireless communication to report, track, monitor, message, relay information and so forth, these devices may be part of computer system 200.

Computer system 200 may include a bus 202 or other communication mechanisms for communicating information data, signals, and information between various components of computer system 200. Components include an input/output (I/O) controller 204 that processes a user action, such as selecting keys from a keypad/keyboard, selecting one or more buttons, links, actuatable elements, etc., and sends a corresponding signal to bus 202. I/O controller 204 may also be communicatively coupled to an output component, such as a display 206 and a cursor control 208 (such as a keyboard, keypad, mouse, touchscreen, etc.). In some examples, I/O controller 204 may include an image sensor for capturing images and/or video, such as a complementary metal-oxide semiconductor (CMOS) image sensor, and/or the like. An audio I/O component 210 may also be included to allow a user to input voice information that may be converted to audio signals that may be interpreted as commands and/or recordable data. Audio I/O component 210 may allow the user to hear audio. In this regard, the audio I/O component may be a microphone(s)/speaker(s).

A transceiver or network interface 212 transmits and receives signals between computer system 200 and other devices, such as another user device, a service provider server, an email server, application service provider, web server, a healthcare provider server, and/or other servers via a network. In various embodiments, such as for many cellular telephone and other mobile device embodiments, this transmission may be wireless, although other transmission mediums and methods may also be suitable. A processor 214, which may be a micro-controller, digital signal processor (DSP), or other processing component, processes these various signals, such as for display on computer system 200 or transmission to other devices over a network 108 via a communication link 218. Communication link 218 may be a wireless communication in some embodiments. Processor 214 may also control transmission of information, such as cookies, IP addresses, images, videos, and/or other data to other devices.

Components of computer system 200 also include a system memory 220 (e.g., RAM), a static storage component 222 (e.g., ROM), and/or a disk drive 224. Computer system 200 performs specific operations by processor 214 and other components by executing one or more sequences of instructions contained in system memory 220. Logic may be encoded in a computer-readable medium, which may refer to any medium that participates in providing instructions to processor 214 for execution. Such a medium may take many forms, including but not limited to, non-volatile media, volatile media, and/or transmission media. In various implementations, non-volatile media includes optical or magnetic disks, volatile media includes dynamic memory such as system memory 220, and transmission media includes coaxial cables, copper wire, and fiber optics, including wires that comprise bus 202. In one embodiment, the logic is encoded in a non-transitory machine-readable medium. In one example, transmission media may take the form of acoustic or light waves, such as those generated during radio wave, optical, and infrared data communications.

Some common forms of computer readable media include, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, or any other medium from which a computer is adapted to read.

In various embodiments of the present disclosure, execution of instruction sequences to practice the present disclosure may be performed by computer system 200. In various other embodiments of the present disclosure, a plurality of computer systems 200 coupled by communication link 218 to the network (e.g., such as a LAN, WLAN, PTSN, and/or various other wired or wireless networks, including telecommunications, mobile, and cellular phone networks) may perform instruction sequences to practice the present disclosure in coordination with one another. Modules described herein may be embodied in one or more computer readable media or be in communication with one or more processors to execute or process the techniques and algorithms described herein.

A computer system may transmit and receive messages, data, information and instructions, including one or more programs (i.e., application code) through a communication link and a communication interface. Received program code may be executed by a processor as received and/or stored in a disk drive component or some other non-volatile storage component for execution.

Where applicable, various embodiments provided by the present disclosure may be implemented using hardware, software, or combinations of hardware and software. Also, where applicable, the various hardware components and/or software components set forth herein may be combined into composite components comprising software, hardware, and/or both without departing from the spirit of the present disclosure. Where applicable, the various hardware components and/or software components set forth herein may be separated into sub-components comprising software, hardware, or both without departing from the scope of the present disclosure. In addition, where applicable, it is contemplated that software components may be implemented as hardware components and vice-versa.

Software, in accordance with the present disclosure, such as program code and/or data, may be stored on one or more computer-readable media. It is also contemplated that software identified herein may be implemented using one or more computers and/or computer systems, networked and/or otherwise. Such software may be stored and/or used at one or more locations along or throughout the system, at client 102, network-based system 110, or both. Where applicable, the ordering of various steps described herein may be changed, combined into composite steps, and/or separated into sub-steps to provide features described herein.

The foregoing networks, systems, devices, and numerous variations thereof may be used to implement one or more services, such as the services discussed above and in further detail below.

Figure 3:
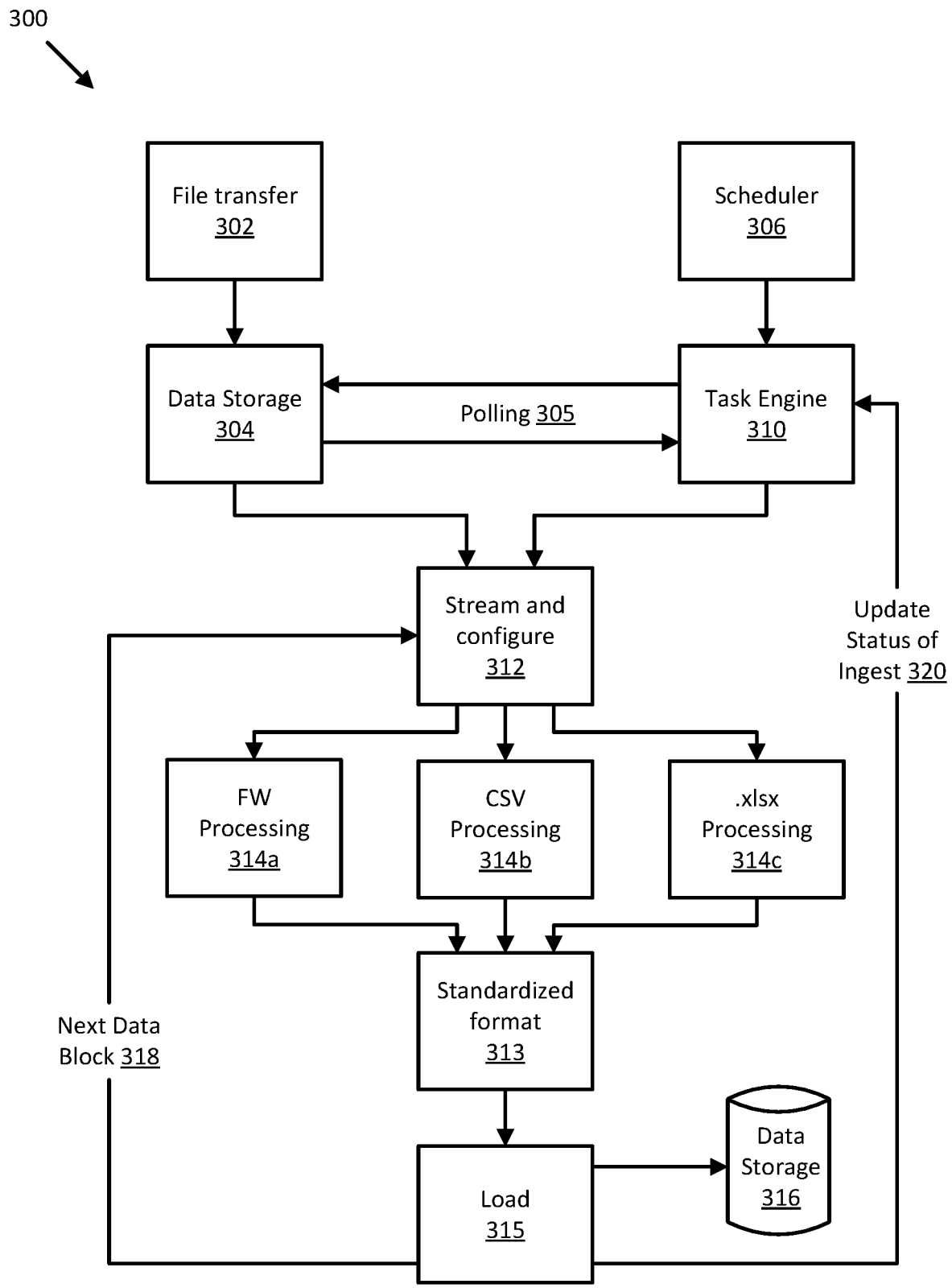
FIG. 3 illustrates a flow diagram of a process for data file processing in accordance with one or more embodiments of the present disclosure.

FIG. 3 illustrates a flow diagram of a process 300 for data file processing (e.g., data ingestion) in accordance with one or more embodiments of the present disclosure. For explanatory purposes, process 300 is primarily described herein with reference to FIGS. 1 and 2. The blocks of process 300 are described herein as occurring in serial, or linearly (e.g., one after another). However, multiple blocks of process 300 may occur in parallel. In addition, the blocks of process 300 need not be performed in the order shown and/or one or more of the blocks of process 300 need not be performed.

At block 302, a system receives raw data files via SFTP, for example, from one or more service providers such as a healthcare or healthcare related service provider. The raw data files may be stored in a data storage 304. Data storage 304 may be a local storage device(s) and/or a cloud storage device(s).

Task engine 310 may have a scheduler component 306 (e.g., celerybeat) that may be utilized to initiate a task of polling 305 data storage 304 at regular intervals to identify new raw data files received from the service provider. The frequency of polling 305 for new raw data files may be periodic such as hourly, daily, weekly, or implemented as needed to suit a desired application of an embodiment. If new raw data files are detected in a poll for new data files, task engine 310 may obtain/retrieve the new raw data files for data file processing. In some embodiments, task engine 310 detects new raw data files by comparing the new raw data files to records indicating already processed data files. File attributes of a data file such as a timestamp, file name, file size, etc., may be compared to file attributes of already processed files (having a status indicating processing has already been successfully completed) to determine whether the data file is a new data file that should be processed. For example, a new file having a matching name and timestamp as a file that has already been processed may be determined to be a duplicate file that does not need to be processed.

In some embodiments, task engine 310 polls the healthcare or healthcare related service provider directly for the raw data files via SFTP. In this regard, task engine 310 may actively retrieve raw data files from the healthcare or healthcare related service providers at regular/predefined intervals such as those above.

At block 312, the raw data files are streamed from data storage 304 in configurable sized data blocks for individual processing. For example, a file containing a large number of rows of data may be configured into a plurality of data blocks, where each data block contains a subset number of rows. In this regard, each data block may be a chunk of the entire dataset of the file. In some embodiments, task engine 310 may determine an optimal configuration for chunking the data file based on file size and/or file type. For example, task engine 310 may determine a chunk size based on a number of rows and/or columns of a file. For example, a file containing 100 rows may be separated into 5 chunks each containing 20 rows of the file. As another example, a file containing 1000 rows may be separated into 10 chunks each containing 100 rows of the file.

As another example, a file having a file type such as a Microsoft Excel Open XML Format Spreadsheet Excel file (XLSX) may be separated into smaller chunks than a comma-separated values files CSV file as the XLSX file may require more computational resources to process (e.g., additional plug-ins). In some embodiments, task engine 310 may be trained using machine learning to optimize determining chunk sizes for the data blocks. For example, characteristics of data files and the time spent processing the data files may be stored as training data sets to learn from. In an implementation, a classification and regression tree may be implemented as part of a process for determining chunk size for incoming data files.

It will be appreciated that chunking the raw data files into data blocks allows for processing large files without over-using memory. A subset of the large file may be processed, and after finishing the subset, a next subset of the large file may be processed and so forth until the large file has been completely processed. Thus, the memory usage required to process a large file can be reduced to a usage required to process a subset of the large file.

At blocks 314*a*-*c*, the system processes the data blocks of the raw data files. To process the data blocks, a schema corresponding to each file type may be used to map data from the data block into a data object 313 having a standardized format. For example, comma-separated value files (e.g., CSV, .txt), Microsoft Excel Open XML Format Spreadsheet Excel files (e.g., XLSX), and fixed width (FW) files may each have a different corresponding schema that may be used to extract information from data blocks of these files and map the information to data object 313 having a standardized format. Thus, regardless of the file type, the present disclosure provides for a standardizing process that allows for remote users to share information that can be aggregated into a standard format such that the information may be evaluated by a central processing entity to determine hidden insights from the large volume of data.

At block 315, the data block that has been standardized into data object 313 is loaded into data storage 316. The system may iterate through each data block (iteration denoted as 318 in FIG. 3) until all of the data blocks have been processed for the new raw data file. The data objects 313 in data storage 316 may be utilized for reporting access and various other machine intelligence operations further described below.

After each data block has been processed, standardized, and loaded to data storage 316, the system may update a status of the ingestion process (update denoted as 320 in FIG. 3). For example, the updated status may include digitally recording an indication that a new file has successfully been processed and loaded into data storage 316. The record indicating that the new file has been processed may be used in the comparison as discussed above to determine whether incoming files are new or have already been processed. Thus, duplicate processing may be avoided, and computing resources may be preserved.

A data file may contain information related to the healthcare provider that sent the data file. For example, a data file may be for claims, inpatient census, pre-authorization, case management, utilization management, 271 files, and/or prescription claims history associated with the health care provider and its patients.

A claims data file may be a file containing claims that have been filed against the healthcare service provider by plan holders. For example, a claim may be a formal request by the plan holder for coverage or compensation for a covered event of the plan. In some embodiments, a claims data file may be used to identify and predict high-risk conditions in a patient population, thereby enabling timely intervention to improve individuals' health. For example, specific diagnosis codes for diabetes with claims data files can be tracked over time for a patient or set of patients to monitor the progression of diabetes for the patient or set of patients.

An inpatient census data file may contain information about patients associated with the healthcare provider. For example, if the health care provider is a hospital, the inpatient census data file may contain information indicating whether a patient is expected to be admitted, whether the patient is admitted, or whether the patient has been discharged. Trends such as readmittance may be used to determine effectiveness of medical interventions and/or whether further medical interventions may assist in preventing future readmittances.

A pre-authorization file may contain information about outpatient procedures. Such outpatient procedures may be used to determine future interventions to provide to patients as follow up protocols.

A case management data file may contain information about all currently open cases that are actively being serviced by a healthcare service provider.

A utilization management data file may be a usage report of health services rendered before, during, and after treatment of a patient.

A compiled 271 file may include all 271 transactions from a healthcare provider within a certain time frame. The 271 transactions may be filtered to determine when patient might be in the emergency room and this may trigger a clinical support protocol for a patient primary care team through automatic mechanisms supported by the appropriate clinical staff.

A prescription claims history file may contain information about a patient's prescription claim history including pharmacy transactions, drug details, and quantities.

In some embodiments, patient profiles stored in the data storage 316 may be updated based on the load/sync operation above. The patient profiles may be retrievable by a unique patient identifier. For example, querying data storage 316 for information corresponding to the unique patient identifier corresponding to a patient profile may provide access to all information associated with the unique patient identifier. Updates to the patient profile may contain information related to monitored progress of the patient profile such as whether the patient took actions in response to a medical intervention provided to the patient (e.g., sent to a user device associated with the patient profile), or updates to one or more health metrics associated with a medical condition for the patient. For example, a body weight measurement and/or blood pressure measurement may be tracked and updated to the patient profile after an in-app notification has been provided to the user suggesting that the user change their diet to include more micronutrient-dense foods.

Incoming data files may include a unique patient identifier that may be tracked such that the information extracted in the data file through the data ingestion process described above may be used to update the patient profile (e.g., by matching the unique patient identifier of the incoming data file to the unique patient identifier of the patient profile, and updating the patient profile with the new information from the data file).

Typically, health care provider computer systems for different health care providers do not maintain a standardized format in which data is stored in their computer systems. This presents a technical challenge in the art of machine intelligence because a machine learning model may not be able to efficiently process the data as an input when the data comprises several different and potentially unknown formats. Thus, process 300 presents a technical solution by allowing data files to be received from disparate sources (e.g., different health care provider computer systems), such that information from the data can be filtered, aggregated, and standardized in process 300, such that the data can be holistically analyzed to determine insights about large populations of patients, or individual patients, who may share similar or the same medical conditions. The insights may not readily be apparent to humans and it may be infeasible for humans to mentally process the large volume of data, however, by using machine intelligence, the insights may be discovered in a time-efficient manner. It will further be appreciated that the aggregation of a large volume of data from disparate sources acts to provide an enhanced pool of data for insight analysis about the large populations of patients with different medical conditions. Additionally, the large volume of data from disparate sources allows for optimal training opportunities for machine learning models to generate more effective decisions in the future. Consequently, machine intelligence performed on the enhanced pool of data may improve over time.

Figure 4:
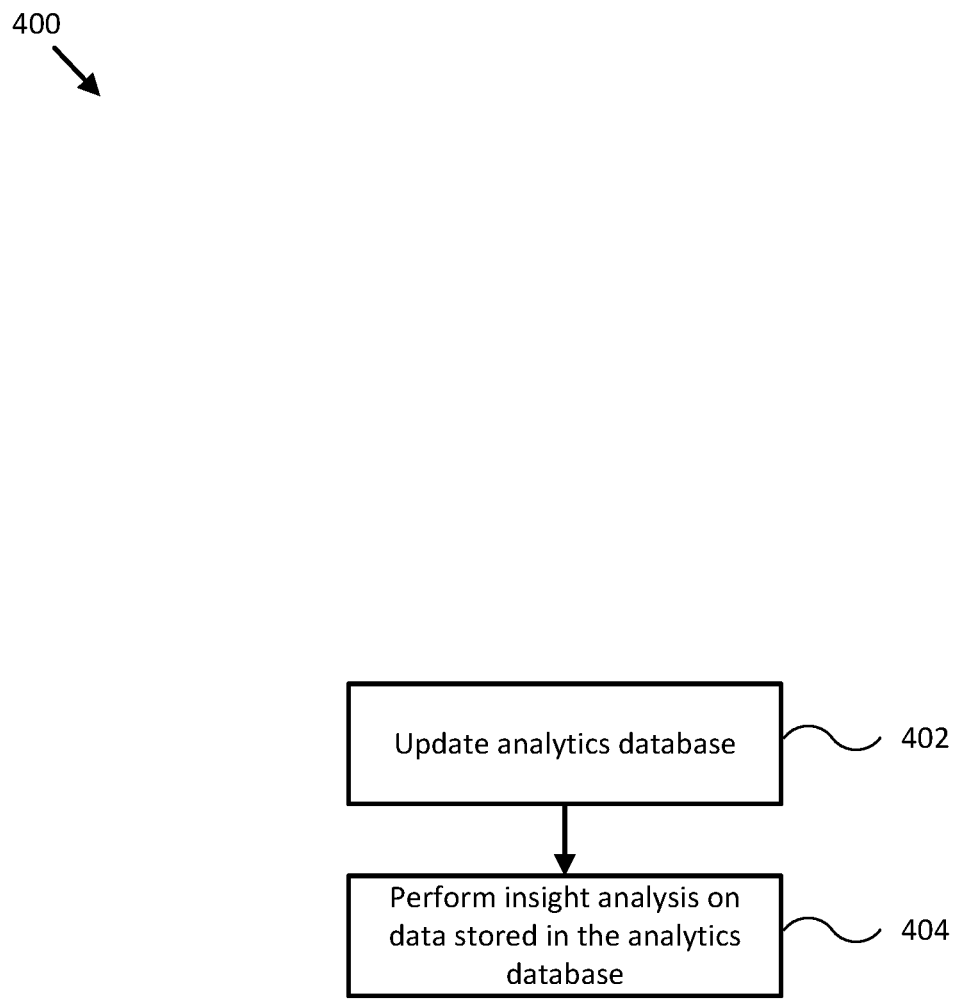
FIG. 4 illustrates a flow diagram of a process for insight analysis using machine intelligence in accordance with one or more embodiments of the present disclosure.

FIG. 4 illustrates a flow diagram of a process 400 for insight analysis using machine intelligence in accordance with one or more embodiments of the present disclosure. For explanatory purposes, process 400 is primarily described herein with reference to FIGS. 1-3. The blocks of process 400 are described herein as occurring in serial, or linearly (e.g., one after another). However, multiple blocks of process 400 may occur in parallel. In addition, the blocks of process 400 need not be performed in the order shown and/or one or more of the blocks of process 400 need not be performed.

At block 402, a system updates an analytics database. In some embodiments, one or more of the operations discussed in reference to process 300 of FIG. 3 may be used to update the analytics database, and the analytics database may be, may be part of, or may include data storage 316 of FIG. 3.

At block 404, the system may use machine intelligence to perform insight analysis on the patient data stored in the analytics database to determine insights related to patient populations/groups.

In one or more embodiments, a unique patient identifier (ID) for a patient profile may be used to link all relevant data for a patient to create the patient profile.

For example, the unique patient ID may be determined to be located in one or more files such as a claims data file as well as a preauthorization data file. Data from the claims data file and the preauthorization data file associated with the unique patient ID may be gathered (e.g., querying the analytics database) and used to generate a patient profile for the patient. A timeline of events may be created from the data files where the timeline of events may be analyzed to determine insight as to how a health condition of the patient has progressed over time in response to interventions and which additional interventions may be provided to the patient to improve the patient's medical condition or bodily health. In some cases, the timeline of events may be part of a patient history for the patient profile.

In various embodiments, individual patient data for a patient profile may be evaluated to determine a group to which the patient profile may be assigned. In some cases, a group may correspond to a certain demographic of people. The system may determine a statistical rate for one or more medical conditions for the group. The statistical rates for the group may be compared to statistical rates of other groups to determine if there are any insights or abnormalities about the group that can be determined. In some cases, if the statistical rate for a medical condition for one or more groups is greater than a predefined threshold above the statistical rate of one or more other groups, the system may identify such to be an insight or abnormality.

As an illustrative example, males who are between the age of 50 to 65 in a certain geographic region may be tracked as a group to determine insights about the group. It may be determined that there is a statistically higher rate of hypertension for males between the ages of 50 and 65 in the certain geographic region when compared to other groups within the certain geographic region.

In various embodiments, health metrics that indicate a state of health of a patient may be analyzed to determine trends or changes in the state of health of the patient. For example, a primary diagnosis code in an inpatient census file associated with a patient may be an ICD code (e.g., ICD-10 code). The ICD-10 code may be compared against a list of ICD-10 codes to determine a corresponding medical classification for the patient. Medical classifications may include diseases, signs and symptoms, abnormal findings, complaints, social circumstances, and external causes of injury or diseases. The system may determine that the state of the patient has changed from a first code to a second code. For example, the first code may indicate that a disease is detected in a patient and the second code may indicate that the disease is no longer detected in the patient. In some embodiments, the changes and trends in the state of the patient may be evaluated in conjunction with past healthcare procedures or activities that the patient may have undergone. In some cases, the patient may have undertaken the healthcare procedures or activities in response to medical interventions or recommendations provided by the system as described below, in which case health metrics may be monitored to determine a progress of recovery and ultimate outcome for the patient.

According to some embodiments, a location of healthcare services rendered to patients may be determined using a place of service code identified in an inpatient census file associated with a patient. The place of service code may be used to track patients that have frequent visits to a location. For example, patients may have a number of visits above a certain threshold of visits to a location associated with an emergency room over a certain period of time. Such patients may be considered high-risk patients for emergency services. High-risk patients may be tracked as a group and healthcare plans may be designed and provided to these patients to reduce their likelihood of visiting the emergency room again in the future.

In one or more embodiments, patient data may be evaluated to determine where healthcare costs can be reduced. For example, brand name drug prescriptions may be compared to generic alternatives to determine if prescription costs can be reduced. As another example, frequently occurring expensive procedures may be reduced in occurrence and/or expense if the patient is educated about effective lifestyle changes.

Figure 5:
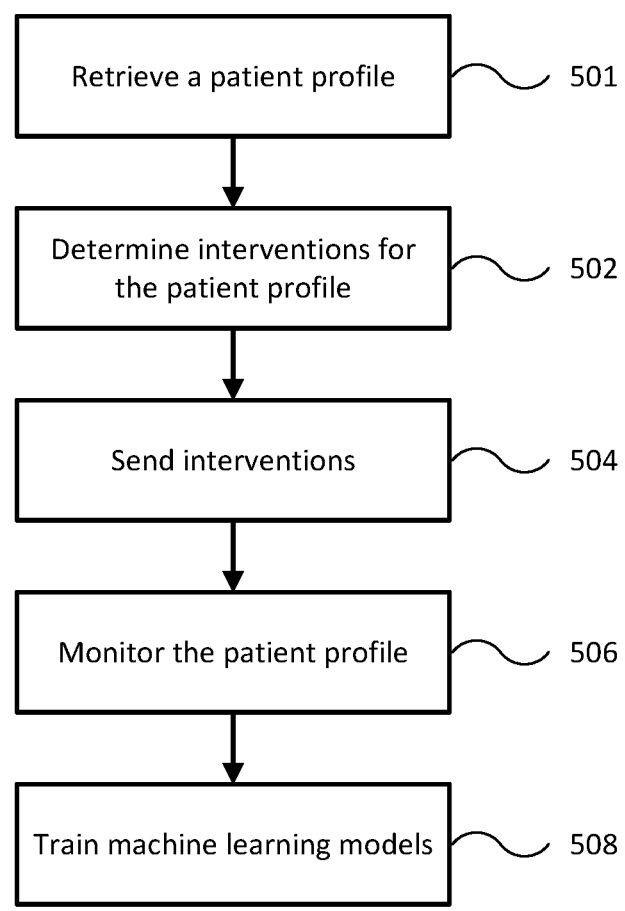
FIG. 5 illustrates a flow diagram of a process for healthcare intervention using machine intelligence in accordance with one or more embodiments of the present disclosure.

FIG. 5 illustrates a flow diagram of a process 500 for healthcare intervention using machine intelligence in accordance with one or more embodiments of the present disclosure. For explanatory purposes, process 500 is primarily described herein with reference to FIGS. 1-4. The blocks of process 500 are described herein as occurring in serial, or linearly (e.g., one after another). However, multiple blocks of process 500 may occur in parallel. In addition, the blocks of process 500 need not be performed in the order shown and/or one or more of the blocks of process 500 need not be performed. In some embodiments, blocks of process 400 may be included in process 500.

At block 501, a system retrieves a patient profile corresponding to a patient. In some embodiments, the patient profile may be retrieved from an analytics database storing the patient profile. In some cases, the patient profile may comprise information from one or more different database tables stored in the database. A unique patient ID for the patient may be used to retrieve the information from the different database tables such that the information may be combined (e.g., selectively gathered) to create the patient profile of a patient. In this regard, the system may match the unique patient ID to an ID in each of the database tables and retrieve any information from the database tables associated with the ID as needed. For example, the retrieval process may be performed by querying the database using the unique patient ID. The database may be a relational database such that the unique patient ID may be used to gather any information about a patient associated with the unique patient ID in a resource efficient manner.

In various embodiments, the patient profile may be accessible and updateable by the patient using an account user interface. For example, the patient may log in to a mobile application or website to update their patient profile. The patient profile may also be updateable by data ingestion as described with respect to process 300 of FIG. 3 where a patient's health care provider may provide new information regarding the patient.

At block 502, the system determines healthcare interventions for a patient profile of a patient population using machine intelligence (e.g., one or more machine learning models). The healthcare interventions may be determined based on one or more healthcare groups to which the patient profile has been assigned. For example, a patient profile may be assigned to a pregnancy group, diabetic group, hypertension group, asthma group, smoker group, specific prescription medicine group, Flu group, ear-ache group, broken bone group, high-risk for emergency room visit group, and/or any other medical condition group for a patient population.

The patient profile may be assigned to one or more groups based on patient data corresponding to the patient profile. For example, the insights determined at block 404 of process 400 may be used to assign the patient profile to a group. As another example, a patient profile may be assigned to a group based on a response to a questionnaire during a patient intake. For example, a response of "yes" to a question of "are you pregnant?" would cause the patient profile to be assigned to the pregnancy group.

As another example, the patient profile may be assigned to a group based on lab results for the patient. For example, a patient profile may be assigned to a pregnancy group after a positive test result for human chorionic gonadotropin (hCG). In this regard, a patient profile's current medical condition can be viewed to determine which group to assign the patient profile. For example, if a current medical condition identified in the patient profile includes "pregnant," then the patient profile may be assigned to the pregnancy group until the medical condition is changed to reflect that the patient is no longer pregnant.

As another example, the patient profile may be assigned to a group based on a claim history associated with the patient profile. The claim history may include claims filed with a healthcare provider by the patient. Each claim may include an ICD code that can be evaluated to determine a current medical condition of the patient. For example, if recent (e.g., within the past three months) claims have an ICD code indicating pregnancy, the patient profile may be assigned to the pregnancy group.

In another example, the patient profile may be assigned to a group based on a real-time video and/or audio teleconference with a physician or other healthcare professional. Voice recognition may be used to analyze a stream of audio transmissions between a patient and a physician during the teleconference to determine a healthcare condition of the patient. For example, during a teleconference, the patient may say "I tested positive on my pregnancy test this morning." The audio may be analyzed to determine if it matches a known audio phrase indicating that a patient is pregnant. If there is a match between the audio and the known audio phrase above a certain confidence threshold, for example, through frequency domain comparison/analysis, the patient profile corresponding to the patient may be assigned to the pregnancy group. In some cases, the system mas assign a patient to a group after receiving input from a physician or healthcare professional about the patient. For example, after a teleconference between a physician and the patient, the physician may send a patient profile update to the system (e.g., using process 300 of FIG. 3) indicating that the patient is pregnant. In response to receiving the update, the system may assign the patient profile to the pregnancy group.

The assignment of a group to a patient profile may be stored in the database and may be readily accessible by querying the database using the unique patent ID.

The determined interventions may vary depending on the patient profile and/or the group to which the patient profile is assigned. One example of an intervention includes awareness campaigns that bring awareness to patients about their medical condition and available healthcare options. An awareness campaign may be a summary of the medical condition and available treatment options or an invitation to take a health screening test (e.g., body mass index (BMI) test). Another example of an intervention includes a notification to a healthcare provider about the medical history of a patient prior to a visit/contact with the healthcare provider. Another example of an intervention includes a telephone call, text message, or email to a patient about their medical condition and available healthcare options. Another example of an intervention includes an in-app notification about healthcare options/benefits or a confirmation request that the recorded medical history of the patient is accurate. Another example of an intervention includes a referral to a health care provider who may assist in treating the medical condition of the patient. Another example of an intervention includes a healthcare kit provision. The healthcare kit may include items and/or devices that may assist the patient in handling their medical condition. For example, a patient with asthma may be provided a healthcare kit with items such as an inhaler or nebulizer.

At block 504, the determined interventions are sent/provided. In some cases, the interventions are sent to a user account associated with the patient profile, a user device (e.g., email address, mobile number, messaging application, mobile app) associated with the patient profile, and/or a healthcare provider associated with the patient profile.

In some embodiments, if the intervention is an awareness campaign, an awareness message may be transmitted to the patient profile such that the awareness message may be viewed on a screen of a user device associated with the patient profile. The awareness message may be an automated telephone call, text message, email, and/or in-app notification that the patient may view and interact with to gain awareness about their medical condition. The awareness message may further provide suggestions that the patient can implement in their life to address their medical condition. The awareness message may further include healthcare options/benefits available to the patient or a confirmation request for the patient to confirm that the recorded medical history in the patient profile for the patient is accurate. The awareness message may further include a referral to a healthcare provider that specializes in the patient's medical condition. In some cases, the referral may be for a second opinion if the prior medical history for the patient indicates that the patient has already received an examination or diagnosis.

In some embodiments, the intervention may be sent to the healthcare provider(s) associated with the patient. For example, the intervention may be an informative message to the healthcare provider where the message provides a medical history of the patient. In some cases, the medical history may be provided prior to a scheduled visit with the healthcare provider. For example, the healthcare provider may be a specialist that is seeing the patient for a first time. In such a case, the specialist may be able to view the medical history of the patient prior to the visit without requiring the patient to manually fill out a patient medical history form.

In various embodiments, the intervention may be a healthcare kit. In some embodiments, the healthcare kit may be directly shipped to an address associated with the patient profile after electronic acceptance is received from the patient. In some embodiments, the healthcare kit may include hyperlinks to items and/or devices in the healthcare kit that can be purchased by the patient online.

At block 506, the patient profile is monitored. Subsequent to the intervention, the patient profile may be monitored to determine an outcome and/or intermediate changes to one or more health metrics related to the medical condition of the patient as a result of the intervention provided at block 504. For example, if the intervention was a referral to a specialist, the patient profile will be monitored to determine whether the patient scheduled and attends a visit with the specialist and whether the patient's medical condition improves after the visit. In one or more embodiments, the changes may be evaluated to determine trends in the health metrics such as increasing, decreasing, or remaining the same. The intervention and monitored changes may be useful as part of training examples to re-train a machine learning model for further intervention decisions.

The patient profile may be monitored in various ways according to some implementations. For example, if the patient visits the specialist, the patient profile may be updated according to process 300 of FIG. 3 and/or process 400 of FIG. 4. Additionally, devices associated with the patient may be used to receive updates or changes about the patient's medical condition or health. For example, a smart watch, smart scale, user device communicatively linked to a health monitoring device, and/or other wearable health monitoring devices may be used to monitor the patient's health metrics subsequent to the intervention. For example, a patient profile may be automatically updated by an application installed in the patient's user device that monitors the patient's health by connecting to one or more health monitoring devices. For example, the patient may perform an at-home blood test and the raw data may be uploaded to their patient profile automatically using a device that takes the blood sample as input and connects to the application on the user device to upload raw data about the blood sample to the patient profile. The raw data may be analyzed to determine whether the patient has shown improvement in their medical condition. As another example, a patient's smart watch may be used to track a heart rate of the patient, sun exposure endured by the patient, environmental sounds endured by the patient, calories burned by the patient, movement or physical activity (e.g., moving steps) of the patient, which may be uploaded to the patient's patient profile.

Changes in monitored health metric(s) for a patient profile may be used to provide additional interventions. A first health metric value measured at a time before an intervention and a second health metric value measured at a time after the intervention may be compared to determine if there is a positive or negative change in the health metric. In some cases, a negative change may induce another intervention that is more significant than the first intervention such as referring the patient to a specialist or offering healthcare devices for managing the medical condition. A positive change may induce another intervention that is less significant than the first intervention. For example, an awareness campaign message may be less significant of an intervention than a referral to a specialist.

In an example use case, a patient may be diagnosed with high blood pressure. A first intervention of generating a digital recommendation to be sent to the patient's user device suggesting that the patient exercise three times per week may be categorized as less significant than a second intervention of a digital calendar invitation sent to the user device requesting that the patient participate in a video conference visit with a specialist to discuss the high blood pressure. The patient's blood pressure may be monitored and if the blood pressure continues to increase, for example, by a threshold percentage more than the previous measure of blood pressure, then the second intervention may be sent to the patient.

In another example use case, a patient may be diagnosed to be at risk for diabetes. Based on the risk for diabetes, a first intervention may be sent to the patient where the first intervention contains information related to diabetes and suggestions that the patient may incorporate into their lifestyle to reduce the risk for diabetes. For example, the intervention may include a recommendation of physical activity for thirty minutes per day such that a heart rate is elevated to above a threshold beats per minute. A health monitoring device connected to the internet may upload the heart activity of the patient. The heart activity may be analyzed to determine whether the patient has been performing the recommended physical activity. If the patient has been performing the recommended physical activity based on the analyzed heart activity, a second intervention may not be needed. However, if the patient has not been performing the recommended physical activity based on the analyzed heart activity, a second intervention that is more significant than the first intervention may be sent to the patient. For example, the second intervention in this case may be a request to participate in a virtual visit with a healthcare professional.

Incremental changes to one or more health metrics over a period of time may be analyzed to determine trends in the one or more health metrics according to some embodiments. For example, a change in blood pressure may be positive at three different measurement time instances, which may indicate a positive trend. Interventions that may have been provided to the patient profile may be deemed as providing a successful outcome if a positive trend is observed. One or more changes, trends, interventions may be used in creating training examples to further train machine learning models to provide better interventions in the future for a patient population.

At block 508, the machine learning models may be trained (e.g., re-trained, updated). The interventions and the monitored outcomes for patients may be used as new training data examples for the machine learning models to improve how interventions are determined. For example, if an intervention is proven to be effective in treating a patient with a high-risk for emergency room visits, the machine learning models may use data related to that intervention and the positive outcome as a training example for future interventions for other patients who are at a high-risk for emergency room visits.

In this regard, the data sets represent a historical representation of all the medical care that an individual has received (e.g. data collected from claims made by the individual) along with real-time events (e.g. inpatient census datafiles), which can be combined with the individual's electronic health record as well as monitored information like vitals (e.g. via smart device health monitoring applications such as Apple® HealthKit) and the individual's current geo-location and previous geo-locations where health services were received. In one example, a smart device may be used to monitor information such as sleep, cadence of breathing, fall detection, heart rate and electrical pulses, steps walked throughout the day, movement activity versus non-movement activity, distance traveled over certain periods of time, pace, calories burned, etc., each of which may be used in training the machine learning models to determine meaningful interventions.

For example, given this large amount of information about the individual, the system (e.g., machine learning model(s)) may predict the likelihood of events such as emergency room visits, for example, and may recommend a virtual treatment such as an intervention as described herein to prevent the event or provide a plan for the event.

The system may also predict the effectiveness of a treatment for a given service provider site, so that further referrals may be sent to the more effective sites. For example, if a site has a success rate of treating individuals with a certain medical condition that is greater than other nearby sites (e.g., comparing sites within a predetermined region), then interventions sent to individuals in the predetermined region will be recommended the site with a greatest success rate in treating respective medical conditions of the individuals.

It will be appreciated that in some implementations, machine learning may be used for stratification of which patient profiles to engage. For example, based on learned data, a probability for successful intervention may be calculated and used in determining which patient profiles to prioritize in engagement. For example, a patient profile may have certain characteristics that may be used as indications that corresponding interventions or notification would more likely be successful or effective. As an illustrative example, an intervention for a patient profile with characteristics associated with a pregnancy group may be more receptive to an intervention or notification than a patient profile with characteristics associated with an at-risk for diabetes group, or vice versa. As such, interventions for one group of patient profiles may be prioritized over another group of patient profiles.

In another implementation, machine learning may be used to determine which modality for a given type of patient gives a highest probability of engaging the same type of patient in the future. Further, machine learning may be used to determine what content provided to a given type of patient results in a highest probability of engaging the same type of patient in the future.

In some embodiments, claims data may be gathered as discussed herein and integrated with machine intelligence to detect early warning signs for potential comorbidities. For example, from claims data, where one medical condition becomes known, a presence of one or more additional medical conditions may be predicted. As an illustrative example, with a large amount of data, where patients have sequential diagnoses of medical conditions, a machine learning model may determine patterns that allow for predictions of a future medical diagnosis for a patient when the patient has already been diagnosed with certain conditions in the past.

In additional embodiments, machine learning may be used to improve wait times by continually analyzing discrete intake data and length of time for medical visits. For example, predictions can be made for how long a medical visit will take in terms of time and for a particular reason such as checkup, consultation, surgical procedure, and other reasons for medical visit. Thus, wait times may be a variable when determining which interventions to provide to a patient profile. For example, interventions requiring a longer wait time may be less likely to be provided to a patient profile with a dire condition over an intervention with a shorter wait time. Conversely, a patient profile with a mild or less severe condition may be provided with an intervention having a longer wait time but better success rate.

As such, various machine learning algorithms and models that have been trained to provide healthcare interventions may be utilized in one or more of the implementations discussed in the disclosure. As the number of training examples increases, the effectiveness of the machine learning model interventions may improve as the machine learning model will have more data to learn from such as by making make stronger correlations. In this regard, by utilizing a large amount of data gathering, machine learning may continuously refine treatment plans and patient suggestions.

As a use case example, a patient may have a high risk for emergency room visits because the patient has visited the emergency room a certain amount of times over a predefined period of time (e.g., four times in the past month). Accordingly, an intervention may be sent to the patient where the intervention provides a recommendation that the patient visit with a specialist to evaluate their condition (e.g., a virtual visit via video conference). Whether the patient visits the specialist may be monitored. If the patient visits the specialist, and the number of emergency room visits following the visit is determined to be less than before the visit, the case may be used as a training data example for a positive outcome. Thus, data related to the patient such as the patient's medical condition, health metrics, which specialist the patient visited, and so forth (as discussed above), as well as the positive result may be used as a training data example from which a machine learning model may learn.

The foregoing disclosure is not intended to limit the present disclosure to the precise forms or particular fields of use disclosed. As such, it is contemplated that various alternate embodiments and/or modifications to the present disclosure, whether explicitly described or implied herein, are possible in light of the disclosure. Having thus described embodiments of the present disclosure, persons of ordinary skill in the art will recognize that changes may be made in form and detail without departing from the scope of the present disclosure.

What is claimed is:

1. A system, comprising:
  a non-transitory memory; and
  one or more hardware processors coupled to the non-transitory memory and configured to read instructions from the non-transitory memory to cause the system to perform operations comprising:
  receiving data associated with a medical condition from a user;
  based on the user, retrieving a patient profile from a database storing the patient profile;
  determining an intervention for the medical condition based on a patient history associated with the patient profile provided as an input to a machine learning model trained to provide recommended interventions;
  sending the intervention to a user device associated with the user for display on a graphical user interface of the user device;
  monitoring for changes in one or more health metrics associated with the user by:
    polling a data storage for new raw data files transferred from one or more computer systems associated with health care service providers;
    retrieving a raw data file from the data storage;
    converting the raw data file into data that is in a standardized format, wherein the converting is based on a type of the raw data file and a conversion schema corresponding to the type of the raw data file;
    loading the converted data to the patient profile; and
    identifying one or more trends in the one or more health metrics based at least in part on the loading of the converted data to the patient profile; and
  re-training the machine learning model, for predicting future recommended interventions, based on the sent intervention and the identified one or more trends in the one or more health metrics.

2. The system of claim 1, wherein the patient profile includes an assigned group of a plurality of groups, wherein each of the plurality of groups corresponds to a medical condition.

3. The system of claim 2, wherein the intervention comprises an in-app notification that includes information about the medical condition.

4. The system of claim 1, wherein the changes are from a first health metric value measured before the intervention to a second health metric value measured after the intervention.

5. The system of claim 1, wherein the operations further comprise:
  polling one or more devices associated with the patient profile for updates to the one or more health metrics.

6. The system of claim 5, wherein the one or more devices includes a sphygmomanometer configured to measure a blood pressure of a patient associated with the patient profile.

7. The system of claim 1, wherein the operations further comprise:
  determining a second intervention based on the changes in the one or more health metrics; and
  sending the second intervention to the user device associated with the patient profile for display on the graphical user interface of the user device.

8. The system of claim 7, wherein the operations further comprise determining a negative trend based on the changes, and wherein the determining the second intervention is in response to the determining the negative trend.

9. The system of claim 1, wherein the patient profile is for the user.

10. The system of claim 1, wherein the patient profile is for a patient different than the user.

11. A method comprising:
receiving data associated with a medical condition from a user;
based on the user, accessing a patient profile from a database in which the patient profile is stored;
inputting a patient history associated with the patient profile to a machine learning model trained based on aggregated patient data;
outputting an intervention for the patient profile from the machine learning model;
sending the intervention to a user device associated with the patient profile for display on a graphical user interface of the user device;
monitoring the patient profile for changes in one or more health metrics by:
polling a data storage for new raw data files transferred from one or more computer systems associated with health care service providers;
retrieving a raw data file from the data storage;
converting the raw data file into data that is in a standardized format, wherein the converting is based on a type of the raw data file and a conversion schema corresponding to the type of the raw data file;
loading the converted data to the patient profile; and
identifying one or more trends in the one or more health metrics based at least in part on the loading of the converted data to the patient profile; and
creating a training example based on the monitoring and the intervention.

12. The method of claim 11, further comprising training the machine learning model using the created training example.

13. The method of claim 11, further comprising polling the user device for updates to the one or more health metrics.

14. The method of claim 13, wherein the polling is performed at predefined intervals based on the medical condition.

15. The method of claim 11, further comprising:
receiving a first health metric value;
receiving a second health metric value; and
determining a change in the one or more health metrics when the second health metric value is greater than or less than the first health metric value, wherein the change is part of the identified one or more trends.

16. A non-transitory machine-readable medium having stored thereon machine-readable instructions executable to cause a machine to perform operations comprising:
obtaining a patient profile from a database;
inputting the patient profile to a machine learning model to determine an intervention for the patient profile based on a patient group to which the patient profile has been assigned, wherein the machine learning model has been trained to provide interventions for patient groups based on characteristics of the patient groups;
sending the intervention to a user device associated with the patient profile for display on a graphical user interface of the user device;
subsequent to the intervention, monitoring the patient profile for changes in one or more health metrics by:
polling a data storage for new raw data files transferred from one or more computer systems associated with health care service providers;
retrieving a raw data file from the data storage;
converting the raw data file into data that is in a standardized format, wherein the converting is based on a type of the raw data file and a conversion schema corresponding to the type of the raw data file;
loading the converted data to the patient profile; and
identifying one or more trends in the one or more health metrics based at least in part on the loading of the converted data to the patient profile; and
re-training the machine learning model based on the intervention and the identified one or more trends in the one or more health metrics.

17. The non-transitory machine-readable medium of claim 16, wherein the intervention is at least one of an automatically generated email, text message, or telephone call containing information related to the intervention.

18. The non-transitory machine-readable medium of claim 16, wherein the monitoring for changes comprises retrieving a user action uploaded to the patient profile and one or more measured health metric updates.

19. The non-transitory machine-readable medium of claim 18, wherein the user action is at least one of scheduling a medical appointment, changing a diet, or attending a group class.

20. The non-transitory machine-readable medium of claim 18, wherein the one or more measured health metric updates comprises a body weight measurement and a blood pressure measurement.

* * * * *